United States Patent
Ghosh et al.

(10) Patent No.: US 10,510,675 B2
(45) Date of Patent: Dec. 17, 2019

(54) SUBSTRATE STRUCTURE WITH SPATIAL ARRANGEMENT CONFIGURED FOR COUPLING OF SURFACE PLASMONS TO INCIDENT LIGHT

(71) Applicant: GLOBALFOUNDRIES INC., Grand Cayman (KY)

(72) Inventors: Somnath Ghosh, Clifton Park, NY (US); Eswar Ramanathan, Mechanicville, NY (US); Qanit Takmeel, Latham, NY (US); Ming He, San Jose, CA (US); Jeric Sarad, Mechanicville, NY (US); Ashwini Chandrashekar, Clifton Park, NY (US); Colin Bombardier, Clifton Park, NY (US); Anbu Selvam KM Mahalingam, Mechanicville, NY (US); Keith P. Donegan, Saratoga Springs, NY (US); Prakash Periasamy, Fremont, CA (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 42 days.

(21) Appl. No.: 15/888,366

(22) Filed: Feb. 5, 2018

(65) Prior Publication Data

US 2019/0244911 A1 Aug. 8, 2019

(51) Int. Cl.
| | |
|---|---|
| H01L 21/00 | (2006.01) |
| H01L 23/544 | (2006.01) |
| G01N 21/552 | (2014.01) |
| G01B 11/27 | (2006.01) |
| H01L 21/68 | (2006.01) |

(52) U.S. Cl.
CPC .......... *H01L 23/544* (2013.01); *G01B 11/272* (2013.01); *G01N 21/553* (2013.01); *H01L 21/681* (2013.01); *H01L 2223/5442* (2013.01); *H01L 2223/54426* (2013.01)

(58) Field of Classification Search
None
See application file for complete search history.

(56) References Cited

U.S. PATENT DOCUMENTS

| 7,582,538 B2 | 9/2009 | Lu et al. |
| 2003/0224260 A1 | 12/2003 | Ning |

*Primary Examiner* — Reema Patel
(74) *Attorney, Agent, or Firm* — Anthony Canale; Hoffman Warnick LLC (57) ABSTRACT

Embodiments of the disclosure provide a substrate structure for an integrated circuit (IC) structure, including: a first dielectric layer positioned above a semiconductor substrate; a first plurality of trenches extending at least partially into the first dielectric layer from an upper surface of the first dielectric layer; and a first metal formed within the first plurality of trenches, wherein a spatial arrangement of the first plurality of trenches causes coupling of surface plasmons in the first metal to at least one wavelength of an incident light.

7 Claims, 9 Drawing Sheets

SUBSTRATE STRUCTURE WITH SPATIAL ARRANGEMENT CONFIGURED FOR COUPLING OF SURFACE PLASMONS TO INCIDENT LIGHT

BACKGROUND

Technical Field

The present disclosure relates to integrated circuit (IC) structures for overlay alignment in IC fabrication including multiple patterning lithography. More particularly, the present disclosure relates to forming trenches that allow for coupling of surface plasmons in a metal to incident light. Embodiments of the present disclosure include various substrate structures using plasmon-resonant structures, and methods of forming the same.

Related Art

Integrated circuit fabrication requires forming large numbers of interconnected devices, such as transistors, resistors, capacitors, and diodes on the surface of a semiconductor substrate material. These devices are formed in part by selectively depositing and removing multiple design layers of different materials, e.g., semiconductors, insulators, photoresists, masks, etch stop layers, and metals. Fabrication of functional and reliable ICs depends at least partially on accurate alignment between each of these design layers. Some of these design layers may be formed using multiple patterning lithography. As technology nodes continue to shrink, ensuring accurate alignment between layers has become paramount to the fabrication of functional and reliable ICs.

Double patterning lithography is one type of multiple patterning lithography technology that has been in use for some time. Double patterning lithography generally involves placing shapes that are within the same design layer but too close to each other to be assigned to the same mask layer onto two different mask layers in order to satisfy spacing requirements specified in the design layout. These two different mask layers are then used to print one design layer. Other multiple patterning lithography options such as multiple patterning (e.g., triple or quadruple patterning) lithography may use more than two masks. Accurate alignment between the multiple mask layers is also one of several important factors in fabrication of functional and reliable ICs.

Accurate alignment between design layers and mask layers may be accomplished by several means. One of these is forming one or more substrate structures, which may not include functional components of an electronic circuit, on the partially fabricated IC as it is being processed. Lithography scanners may image the substrate structures and adjust the positions of the partially fabricated IC and the mask reticle to bring them into proper alignment with one another before printing. In addition, substrate structures may be imaged after a series of fabrication operations to detect if misaligned features are present, allowing a determination to be made to continue fabrication, conduct rework operations, or discard a defective IC.

One type of substrate structure, sometimes known more specifically as an "overlay mark," may be composed of several linear metal-filled trenches arranged parallel to one another within a dielectric material. The trenches may be arranged in groups where trenches within a group are in close proximity to one another and multiple groups are arranged to form the substrate structure. The metal in these trenches is electrically isolated from the various devices, such as transistors, and may not have any function in the finished IC. Substrate structures may optionally be positioned in kerf lines between individual dies on the semiconductor substrate. The accuracy of imaging substrate structures is at least partially dependent on the contrast between the materials and the background material of the partially fabricated IC. Higher contrast can improve the accuracy of imaging of the substrate structure and thus the accuracy of alignment between the various layers.

SUMMARY

A first aspect of this disclosure is directed to a substrate structure for an integrated circuit (IC) structure, including: a first dielectric layer positioned above a semiconductor substrate; a first plurality of trenches extending at least partially into the first dielectric layer from an upper surface of the first dielectric layer; and a first metal formed within the first plurality of trenches, wherein a spatial arrangement of the first plurality of trenches causes coupling of surface plasmons in the first metal to at least one wavelength of an incident light.

A second aspect of this disclosure is directed to a substrate structure for an integrated circuit (IC) structure including: a first marking region including: a first trench having a longitudinal orientation and formed on an upper surface of a semiconductor substrate, wherein the first trench has a substantially triangular cross-section and wherein each side of the first trench tapers inwardly towards a first lower tip; a second trench having the longitudinal orientation and formed on the upper surface of the semiconductor substrate, wherein the second trench extends substantially in parallel with the first trench, and wherein the second trench has a substantially triangular cross-section, and wherein each side of the second trench tapers inwardly towards a second lower tip; a ridge formed on the upper surface of the semiconductor substrate, wherein the ridge is positioned directly between the first trench and the second trench, and wherein the ridge extends substantially in parallel to both trenches, and wherein the ridge has a substantially triangular cross-section, and wherein each side of the ridge tapers inwardly towards an upper tip; and a metal formed in the first and second trenches of the first marking region.

A third aspect of this disclosure is directed to a method of detecting overlay alignment when fabricating an integrated circuit (IC) structure, the method including: providing a substrate structure, the substrate structure including: a first dielectric layer positioned above a semiconductor substrate; a first plurality of trenches within an upper surface of the first dielectric layer; and a first metal within the first plurality of trenches, wherein a spatial arrangement of the first plurality of trenches causes coupling of surface plasmons in the first metal to at least one wavelength of an incident light; illuminating the substrate structure with a light source including wavelength components which couple with surface plasmons in the first metal, and wherein the illuminating yields focused plasmons within the substrate structure; and detecting the overlay alignment by detecting the incident light reflected from the substrate structure.

The foregoing and other features of this disclosure will be apparent from the following more particular description of embodiments of this disclosure.

BRIEF DESCRIPTION OF THE DRAWINGS

The embodiments of this disclosure will be described in detail, with reference to the following figures, wherein like designations denote like elements.

It is noted that the drawings of this disclosure are not to scale. The drawings are intended to depict only typical aspects of this disclosure, and therefore should not be considered as limiting the scope of this disclosure. In the drawings, like numbering represents like elements between the drawings.

DETAILED DESCRIPTION

In the following description, reference is made to the accompanying drawings that form a part thereof, and in which is shown by way of illustration specific representative embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

This disclosure relates to integrated circuit (IC) structures and fabrication techniques. More particularly, the present disclosure relates to a substrate structure for an IC structure and methods of using the same to provide, e.g., improvements to image contrast, detectability, etc., as compared to conventional substrate structures. Integrated circuits are manufactured employing, among other operations, multiple processing steps that selectively add or remove material in one or more layers formed on a semiconductor substrate. Certain processing steps may entail multiple addition or removal operations on the same layer. Alternatively or additionally, multiple layers may be affected by a single operation or series of operations. Fabrication of functional and reliable ICs depends at least partially on accurate alignment between each of these layers and between each of the operations performed upon the layers.

Accurate alignment between design layers and mask layers may be accomplished by several means. One of these is forming one or more substrate structures on the partially fabricated IC as it is being processed. Processing equipment may image the substrate structure(s) to adjust alignment during processing, or may image substrate structures after a series of fabrication operations to detect if misaligned features are present. One type of substrate structure that is known in the art is composed of several linear metal-filled trenches arranged parallel to one another within a dielectric material.

Conventional methods of forming metal substrate structures can produce trenches with metal fills that are not thick enough to produce good contrast against the background when imaged. Conventional methods may also produce trenches that lack uniformity. Weak contrast or non-uniformity can cause unreliable results when measuring alignment, resulting in defective product or leading to expensive and time-consuming re-work operations. Embodiments of the present disclosure provide for a distinct spatial arrangement of trenches, and metal therein, to provide stronger image contrast at one or more locations in a substrate structure. Although the present disclosure contemplates embodiments of a substrate structure with varying types of spatial arrangements, each substrate structure discussed herein is structured to include sharp corners, edges, and other geometrical features which concentrate light at a particular point or region of metal. This concentration of light may allow for coupling of surface plasmons in metal to incident light, and thus may improve the detectability of a substrate structure. The various embodiments described herein may increase the accuracy of alignment during fabrication, increasing yield and decreasing costs.

Figure 1:
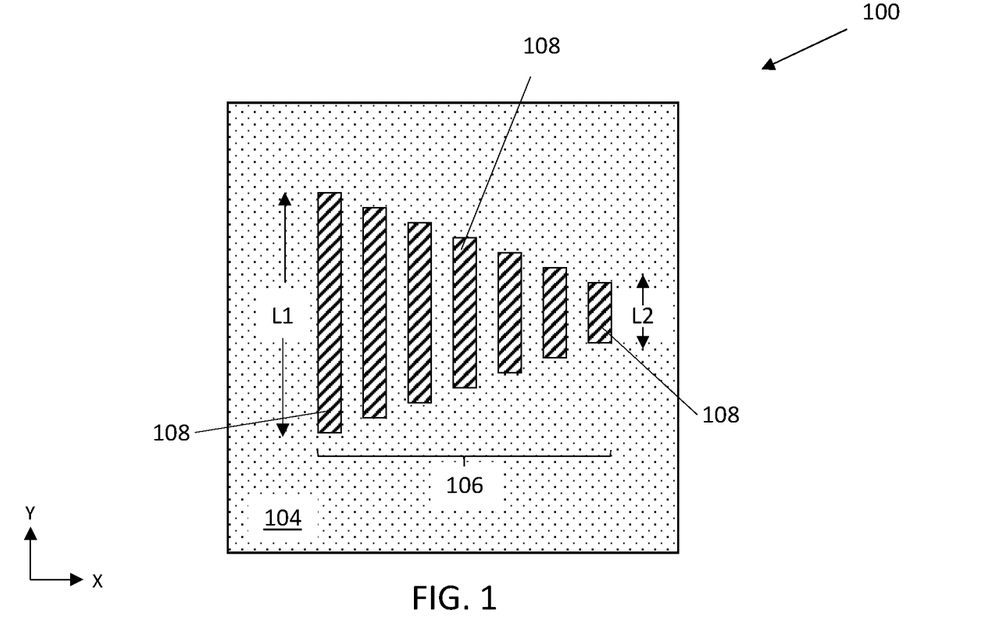
FIG. 1 shows a plan view in plane X-Y of a substrate structure according to embodiments of the disclosure.
Figure 2:
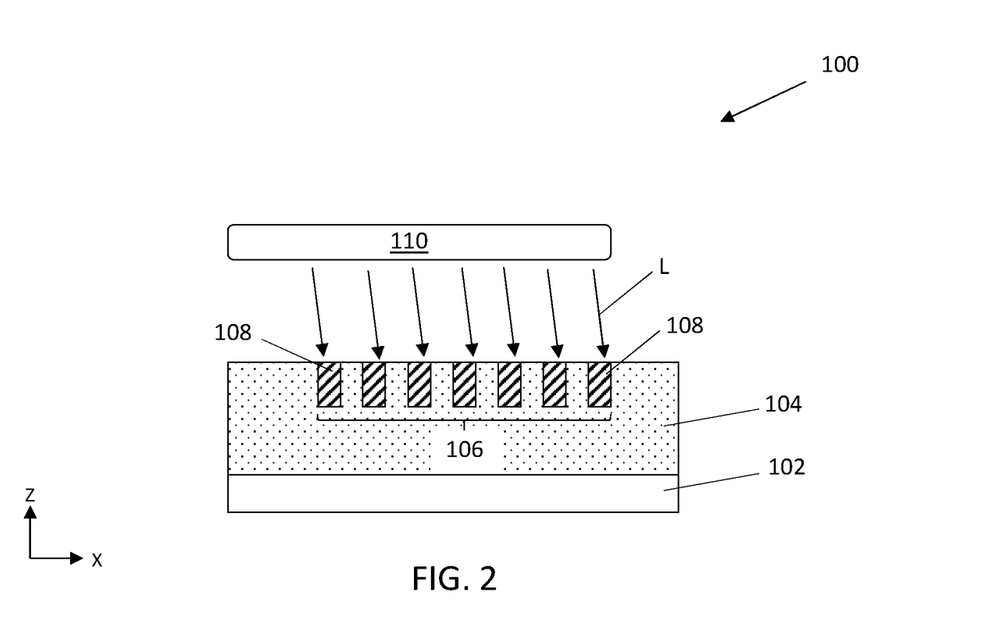
FIG. 2 shows a cross-sectional view in plane X-Z of a substrate structure being illuminated according to embodiments of the disclosure.

Referring to FIGS. 1 and 2 together, a substrate structure 100 according to embodiments of the disclosure is shown. Substrate structure 100 may take a variety of forms, usable together or separately, as described in detail herein to enhance image contrast during analysis of a circuit structure formed to include substrate structure(s) 100 therein. Substrate structure 100 may be embedded within, e.g., a functional or non-functional region of a larger IC device. According to some embodiments, substrate structure 100 may be configured for removal during process steps after detection of substrate structure(s) 100, e.g., by being located within or proximal to a scribe line where individual die are separated from a larger wafer structure. Embodiments of the disclosure may take advantage of physical phenomena arising from the interaction between particular wavelengths of light and one or more surfaces of a metal structure. In particular, embodiments of the disclosure rely upon the excitation of surface plasmons in a particular metal to improve the reflectivity, detection, etc., of one or more structures in an substrate structure.

The overall structure of substrate structure 100 may include a spatial arrangement, defined herein as a combination of one or more shapes, sizes, orientations, etc., of metal components and trenches in substrate structure 100 configured to induce the coupling of surface plasmons to at least one wavelength of incident light transmitted to substrate structure 100. The spatial arrangement of metals in substrate structure 100 may be selected to increase the reflectivity of substrate structure 100 and its components, e.g., by using surface plasmons in the metal to provide greater reflectivity than may be available in conventional substrate structures. In addition, the individual shapes, geometrical profiles, etc., of each spatial arrangement for substrate structure 100 may be chosen to enable the multiplication of plasmon momentum from larger-volume metals to smaller-volume metals. These characteristics of substrate structure 100 may focus plasmon formation on metal surfaces, and increase the intensity of reflected light. Thus, substrate structure may behave similarly to a diffraction grating configured to direct light energy toward smaller regions of metal, where incident light will more easily couple to and excite surface plasmons on particular surfaces or regions of the metal.

To better illustrate the various embodiments of substrate structure 100, an overview of surface plasmon interaction according to the present disclosure is provided. The term "plasmon" does not refer to a particular particle classification, but rather denotes groups of electrons which behave similarly to a single particle when acted upon by particular wavelengths of incident light. The term "surface plasmon" distinguishes surface plasmons appearing at or proximal to the surface of a metal or other structures from plasmons which may be buried beneath other regions, layers, etc., of a metal substance. Surface plasmons may further be defined as groups of delocalized electron oscillations induced along the interface between two or more adjacent materials, and created by photonic energy entering a particular interface by interaction with an incident light. For ease of understanding, plasmons may be considered for the purpose of explanation as an area of electronic "fluid" in a piece of conductive material that may undergo electrical excitation upon being subjected to incident light at a particular wavelength. The resulting surface plasmons in a metal may themselves exhibit a particular wavelength and frequency, which may themselves be dependent upon the wavelength(s) of light being incident upon the surface where surface plasmons form. The resulting frequency and wavelength of surface plasmons may ensue from attractive forces being applied to the excited electrons, caused by non-excited portions of the surface structure pulling the plasmons back to their original positions.

It has been determined that the frequency of some surface plasmons may be similar to that of visible light frequencies. To this extent, embodiments of the present disclosure provide substrate structure(s) 100 with spatial arrangements configured to couple surface plasmons in a metal structure to incident light. The metallic regions of substrate structure 100 may function similarly in principle to a diffraction grating. According to an example, incident light coming into contact with a material having a grating constant K will gain a momentum in multiples of $2\pi/K$ in the direction of the light's periodicity, and thus allow for coupling between particular wavelengths of light and higher-momentum surface plasmons in the metal. The coupling of surface plasmons to incident light, as discussed herein, is particularly desirable in substrate structures configured for detection and analysis by illumination from an external light source. Although various spatial arrangements for substrate structure(s) 100 are described in detail herein, each of the various arrangements is linked by one or more underlying structural features capable of causing the aforementioned coupling of surface plasmons to particular wavelengths of incident light. As will be discussed in various examples herein, substrate structure 100 may include a set of trenches, each filled with metal, in close proximity with each other and decreasing in size along a particular range of surface areas, volumes, etc. It may be desirable for the various trenches and substrate structures 100 to converge upon one or more particular light-concentrating trenches, points, etc., representing the smallest-size element in substrate structure 100. The relative size of such trenches, points, etc., compared to nearby elements of increasing size, relative to the smallest element, creates a focusing effect and corresponding point of concentration for incident light, and thus greater image detection, contrast, etc., through coupling of surface plasmons in a metal to particular wavelengths of incident light. It is therefore understood that although substrate structure(s) 100 are discussed throughout the disclosure with particular types of underlying spatial arrangements, each embodiment of substrate structure(s) 100 is configured to provide coupling between surface plasmons in a metal at a smallest-size element to at least one wavelength of incident light.

In light of the above discussion of interaction between incident light and surface plasmons, methods of using substrate structure 100 for detection of overlay alignment according to the disclosure are discussed herein. Embodiments of the present disclosure include providing an substrate structure 100 of an integrated circuit (IC) to be illuminated during manufacture according to various embodiments. Referring to FIGS. 1 and 2 together, FIG. 1 provides a plan view of an example substrate structure 100, while FIG. 2 provides a cross-sectional view in plane X-Z of substrate structure 100. Substrate structure 100 may include multiple layers fabricated during previous processing steps. For example, substrate structure 100 may include a semiconductor substrate 102 (FIG. 1), a first dielectric layer 104 positioned on semiconductor substrate 102, a first plurality of trenches 106 each filled with a first metal 108, and an external light source 110 (FIG. 2 only) positioned over and in substantial alignment with first metal 108 within first plurality of trenches 106. Light source 110 may emit an incident light L upon substrate structure 100, either directly or after passing through other layers, materials, etc., (not shown) formed on substrate structure 100. It is understood that other materials (not shown) optionally may be included within or proximal to substrate structure 100, e.g., various masks, additional dielectric materials, liners, spacers, etc., but such materials are omitted from the various FIGS. solely for clarity of illustration.

The composition of various materials included within substrate structure 100 may be the same regardless of which particular spatial arrangement(s) are used. For instance, substrate 102 may include materials such as, e.g., silicon, germanium, silicon germanium, silicon carbide, and those consisting essentially of one or more III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and X1+X2+X3+Y1+Y2+Y3+Y4=1 (1 being the total relative mole quantity). Other suitable substrates include II-VI compound semiconductors having a composition $Zn_{A1}Cd_{A2}Se_{B1}Te_{B2}$, where A1, A2, B1, and B2 are relative proportions each greater than or equal to zero and A1+A2+B1+B2=1 (1 being a total mole quantity). Furthermore, the entirety of substrate 102 or various portions of substrate 102 may be strained.

Dielectric materials of first dielectric layer 104 may include any interlevel or intralevel dielectric material including inorganic dielectric materials, organic dielectric materials, or combinations thereof. Dielectric materials may have various dielectric constants (K). High-K dielectrics are employed when high capacitance is desired, and low-K and ultra-low-K dielectrics are employed when low capacitance is desired. Suitable dielectric materials include but are not limited to: carbon-doped silicon dioxide materials; fluorinated silicate glass (FSG); organic polymeric thermoset materials; silicon oxycarbide; SiCOH dielectrics; fluorine doped silicon oxide; spin-on glasses; silsesquioxanes, including hydrogen silsesquioxane (HSQ), methyl silsesquioxane (MSQ) and mixtures or copolymers of HSQ and MSQ; benzocyclobutene (BCB)-based polymer dielectrics, and any silicon-containing low-k dielectric. Examples of spin-on low-k films with SiCOH-type composition using silsesquioxane chemistry include HOSP™ (available from Honeywell), JSR 5109 and 5108 (available from Japan Synthetic Rubber), Zirkon™ (available from Shipley Microelectronics, a division of Rohm and Haas), and porous low-k (ELk) materials (available from Applied Materials). Examples of carbon-doped silicon dioxide materials, or organosilanes, include Black Diamond™ (available from Applied Materials) and Coral™ (available from Lam Research). An example of an HSQ material is FOx™ (available from Dow Corning).

First plurality of trenches 106 of substrate structure 100 may be formed according to any process or combination of processes suitable to form trenches within only targeted regions of first dielectric layer 104. First plurality of trenches 106 in embodiments of substrate structure 100 may differ from similar openings, trenches, etc., in substrate structures by having a spatial arrangement suitable for the coupling of surface plasmons in first metal 108 to particular wavelengths of incident light. Regardless of these structural characteristics of first plurality of trenches 106, first plurality of trenches 106 may be formed by any currently known or later developed process of forming trenches within a dielectric material. For instance, one or more masks (not shown) may be formed on the top of first dielectric layer 104 during manufacture to cover non-targeted portions of first dielectric layer 104, allowing other portions of first dielectric layer 104 to be removed by etching. The mask(s) then may be removed to expose the upper surface of first dielectric layer 104 with first plurality of trenches 106. The various spatial arrangements described herein may be formed, e.g., by changing the mask(s) used to form first plurality of trenches 106.

First metal 108 deposited in first plurality of trenches 106 can be in the form of any currently known or later developed conductive material such as, e.g., aluminum (Al), zinc (Zn), indium (In), copper (Cu), indium copper (InCu), silver (Ag), ruthenium (Ru), tin (Sn), tantalum (Ta), tantalum nitride (TaN), tantalum carbide (TaC), titanium (Ti), titanium nitride (TiN), titanium carbide (TiC), tungsten (W), tungsten nitride (WN), tungsten carbide (WC), cobalt (Co), and/or polysilicon (poly-Si) or combinations thereof. However, some types of metal may exhibit a higher tendency to permit coupling of surface plasmons in the metal to particular wavelengths of incident light. To this extent, embodiments of the disclosure include metal compositions in substrate structure 100 which may not be present in conventional substrate structures and/or not formed to have the various spatial arrangements discussed herein. Such metals particularly suitable for use as first metal 108 may include, e.g., copper (Cu), silver (Ag), ruthenium (Ru), and/or other metals or metal-based substances suitable for the creation of, or use within, metal-to-dielectric interfaces where surface plasmons in the metal may be coupled to particular wavelengths of incident light.

Methods according to the disclosure may include providing substrate structure 100 with a spatial arrangement configured for coupling surface plasmons in first metal 108 to at least one wavelength of incident light (e.g., in the arrangement shown in FIGS. 1, 2 or any of the various arrangements discussed herein), followed by illuminating substrate structure 100 with incident light L from light source 110. As a result of the various physical phenomena discussed herein, illuminating substrate structure 100 with incident light L from light source 110 may yield focused plasmons at the surface of first metal(s) 108 within substrate structure 100. According to the example of FIG. 1, first plurality of trenches 106 includes first metal(s) 108 formed therein, with the various regions of first metal 108 being substantially linear and having a linearly decreasing set of lengths. One first metal 108 (positioned furthest to the left on X-axis), for example, may have a length L1 greater than all other first metals 108 in first plurality of trenches 106. By contrast, another first metal 108 (positioned furthest to the right on X-axis) may have a length L2 that is less than all other first metal 108 in first plurality of trenches 106. Each successive first metal 108 from left to right in first plurality of trenches 106 may exhibit a decreasing length along a particular profile, e.g., until reaching the rightmost first metal 108 with length L2. The spatial arrangement of first metals 108 in first plurality of trenches 106 thus focuses light onto the rightmost first metal 108, and allows coupling of surface plasmons in the rightmost first metal 108 to particular wavelengths of incident light. Thus, the shining of incident light L from light source 110 on substrate structure 100 may cause surface plasmons within first metal(s) 108 to be coupled to particular wavelengths of incident light L for greater detectability of substrate structure 100 within a larger IC structure. Although light source 110 and incident light L are not shown in the various plan views herein, it is understood that each embodiment of substrate structure 100 may be positioned in alignment with light source 110 and incident light L emitted therefrom.

To implement methods according to the disclosure, the settings of light source 110 may be adjustable to yield forms of incident light L capable of inducing greater coupling between surface plasmons of first metal 108 and particular wavelengths of incident light L. According to an embodiment, light source 110 may be selected, configured, etc., to have a wavelength suitable for resonance between the applied incident light L and surface plasmons of first metal 108 when the emitted incident light L is at its highest possible intensity. Stronger resonance between incident light L and first metal 108 may, in some cases, create focused plasmons within first metal 108 of substrate structure 100. To facilitate such a response from first metal(s) 108, light source 110 may be substantially monochromatic (i.e., capable of producing only a subset of wavelengths or colors) to induce resonance between incident light L and first metal 108. Wavelengths of incident light L appropriate for causing surface plasmons of first metal 108 to couple with incident light L may include, e.g., light having a wavelength between approximately four-hundred nanometers (nm) to approximately seven-hundred nm.

The position and/or orientation of light source 110 may also be adjustable to create stronger interaction between incident light L and first metal 108. For instance, the position of light source 110 may be selected, adjusted, etc., to cause incident light L to be substantially perpendicular to the uppermost surface of substrate structure 100 (e.g., the substantially planar upper surface of first dielectric layer 104 and first metal 108). According to further examples, an incident angle of illumination (measured, e.g., relative to the planar upper surface of first dielectric layer 104 and first metal 108) between incident light L and substrate structure 100 may be between approximately five degrees to approximately ninety degrees (i.e., a substantially perpendicular angle). In another subset of embodiments, incident light L may simply be positioned for reflection and detection of at least some incident light L from substrate structure 100.

Figure 3:
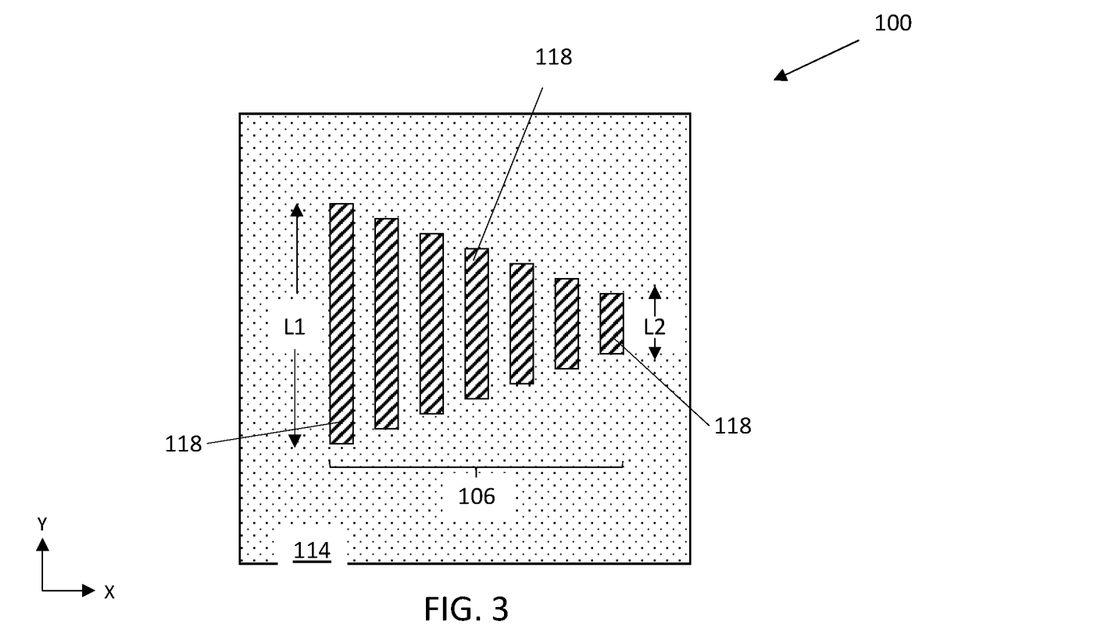
FIG. 3 shows a plan view in plane X-Y of a substrate structure with two vertically aligned layers according to embodiments of the disclosure.
Figure 4:
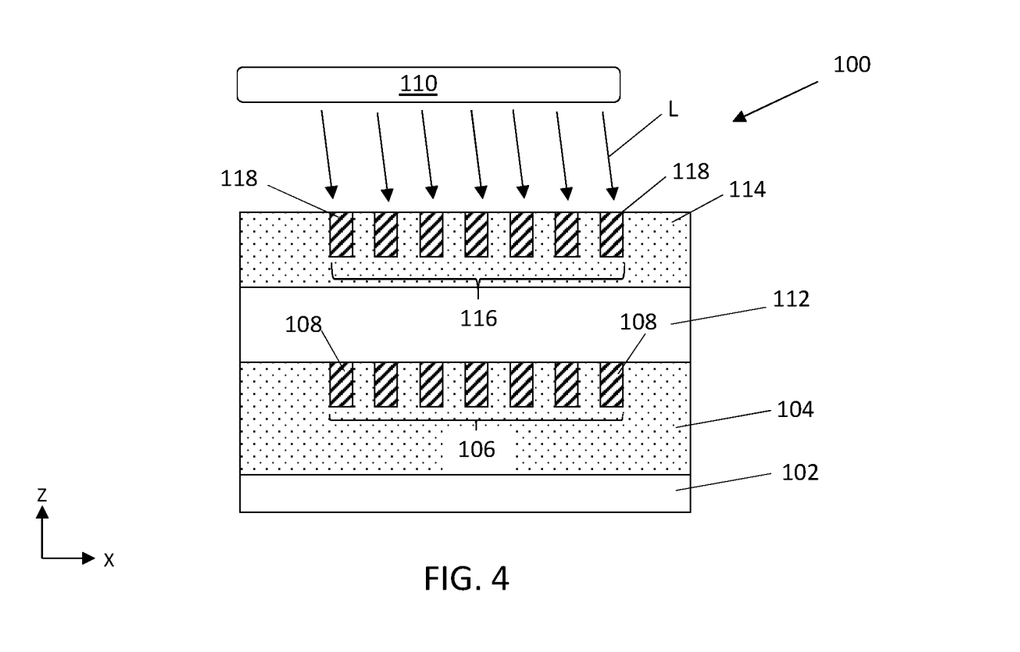
FIG. 4 shows a cross-sectional view in plane X-Z of a substrate structure with two vertically aligned layers according to embodiments of the disclosure.

Proceeding to FIGS. 3 and 4, further embodiments of substrate structure 100 according to the present disclosure are discussed. The various components of substrate structure 100 described herein relative to FIGS. 1 and 2 may form one of multiple reflective elements in a larger structure for determining whether multiple layers of an IC structure are in substantial alignment. According to further embodiments, one or more intermediate layers 112 (FIG. 4 only) may be positioned on or above first dielectric layer 104 and/or first metal(s) 108. Intermediate layer(s) 112 may include one or more semiconductor materials described elsewhere herein, and according to further examples may include one or more of dielectric materials, metals, and/or other materials included within an IC device between various layers or regions of dielectric material. A single intermediate layer 112 is shown in FIG. 4 for the purposes of example, but it is understood that multiple intermediate layers 112 may be included in substrate structure 100 according to various embodiments of the disclosure. A second dielectric layer 114 having, e.g., the same composition as first dielectric layer 104 or other dielectric materials may be positioned on intermediate layer(s) 112. Second dielectric layer 114 may have a second plurality of trenches 116 formed therein.

As discussed in further detail elsewhere herein, second plurality of trenches 116 may exhibit the same spatial arrangement as first plurality of trenches 106, or may exhibit a different spatial arrangement to suit various applications and/or light detection techniques. In any case, second plurality of trenches 116 may be filled with a second metal 118. Second metal 118 may include the same metal as first metal 108 or a different metallic substance, and may have an upper surface substantially coplanar to that of second dielectric layer 114. Incident light L from light source 110 thus may be positioned for coupling to surface plasmons in first and second metals 106, 116. It is also understood that further embodiments of substrate structure 100 may include several additional intermediate layers, dielectric layers, trenches, and metals in addition to intermediate layer 112, second dielectric layer 114, second plurality of trenches 116, second metal(s) 118, to provide detection of multiple layers, regions, etc., of an IC structure. In any case, first and second metals 108, 118 may be substantially vertically aligned with each other, e.g., such that one or more trenches in second plurality of trenches 116 are positioned directly over a corresponding trench of first plurality of trenches 106. Substantial alignment between first and second pluralities of trenches 106, 116 may allow incident light L from the same light source 110 to excite surface plasmons in first and second metals 108, 118 of substrate structure 100.

Figure 5:
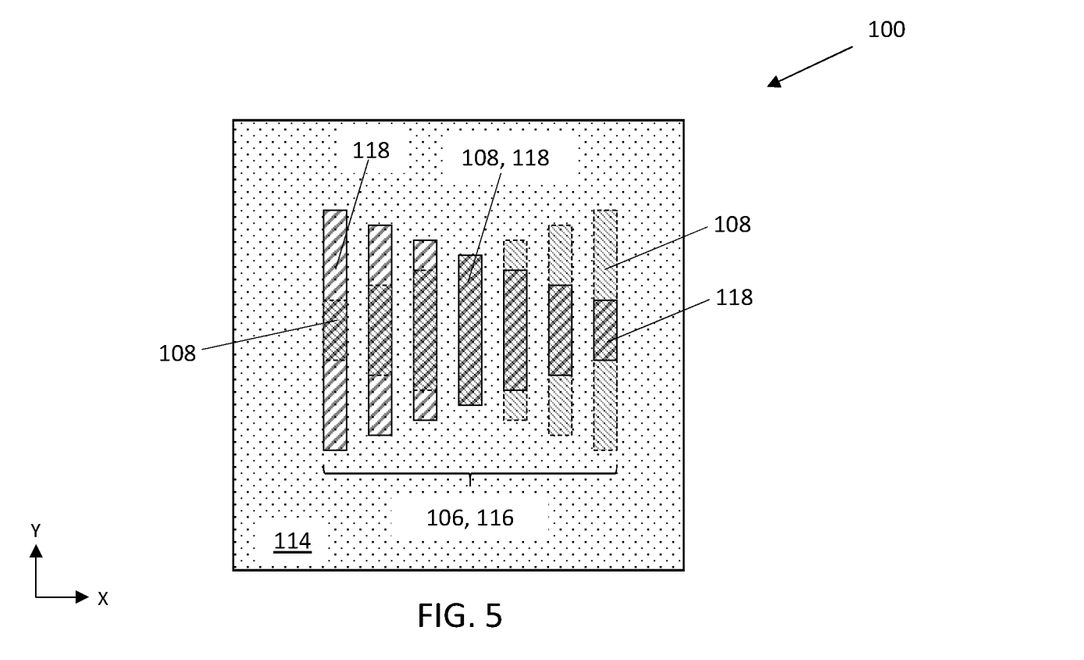
FIG. 5 shows a plan view in plane X-Y of a substrate structure with two vertically aligned and oppositely oriented layers according to embodiments of the disclosure.

Referring to FIGS. 4 and 5 together, some embodiments of substrate structure 100 may include first and second pluralities of trenches 106, 116 with varying orientations. In the plan view of FIG. 5, first plurality of trenches 106 and first metal(s) 108 therein are shown by phantom lines to denote their positions beneath the solid line depiction of second plurality of trenches 116 and second metal(s) 118 therein. In the example of FIG. 4, each plurality of trenches 106, 116 and metal(s) 108, 118 have a same shape and orientation, thereby focusing incident light onto the right side of substrate structure 100 along X-axis. That is, they are aligned over one another as shown in FIG. 3. In the additional example of FIG. 5, each plurality of trenches 106, 116 is structured to concentrate light at one region of metal 106, 108 at opposite locations. Thus, first plurality of trenches 106 is structured to concentrate light at a location opposite that of second plurality of trenches 116, e.g., by the smallest region of metal(s) 108, 118 in each plurality of trenches 106, 116 being positioned at opposite ends relative to each other. In the example of FIG. 5, the leftmost first metal 108 in first plurality of trenches 106 has the smallest length and thus provides the greatest concentration of surface plasmons in first plurality of trenches 106, while the rightmost second metal 118 serves this function in second plurality of trenches 116. The arrangement of FIG. 5 may be preferable in some instances for detecting where substrate structure 100 is formed within each layer where remaining portions of substrate structure 100 have significant surface contrast without relying solely on the coupling of surface plasmons to incident light.

Figure 6:
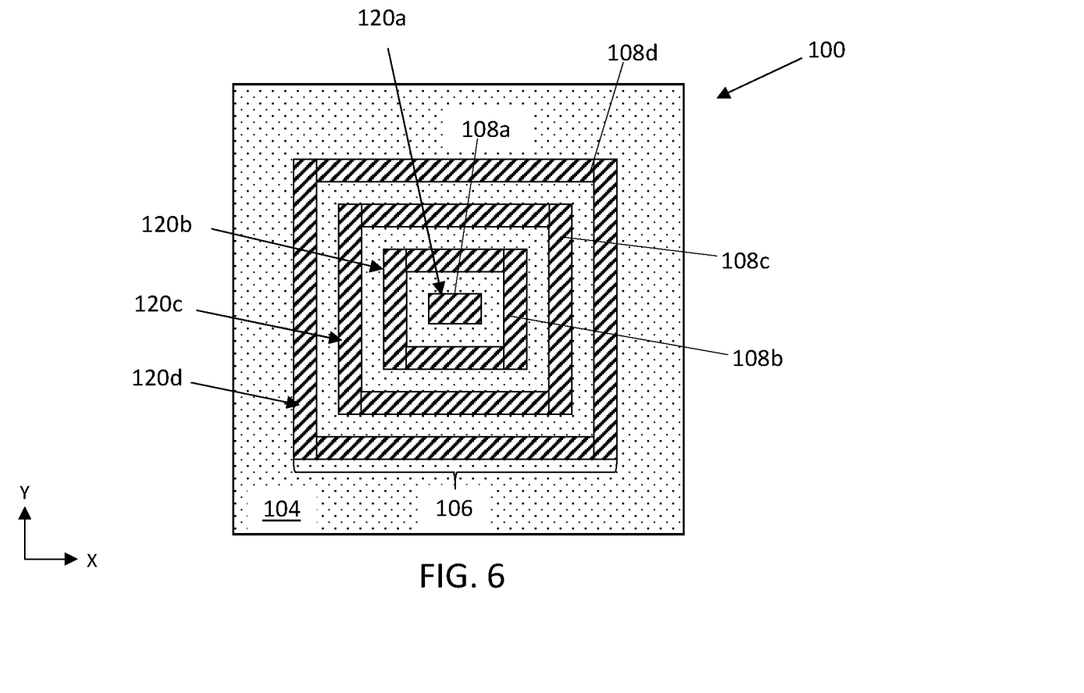
FIG. 6 shows a plan view in plane X-Y of a substrate structure spatial arrangement with multiple quadrilateral trenches according to embodiments of the disclosure.
Figure 7:
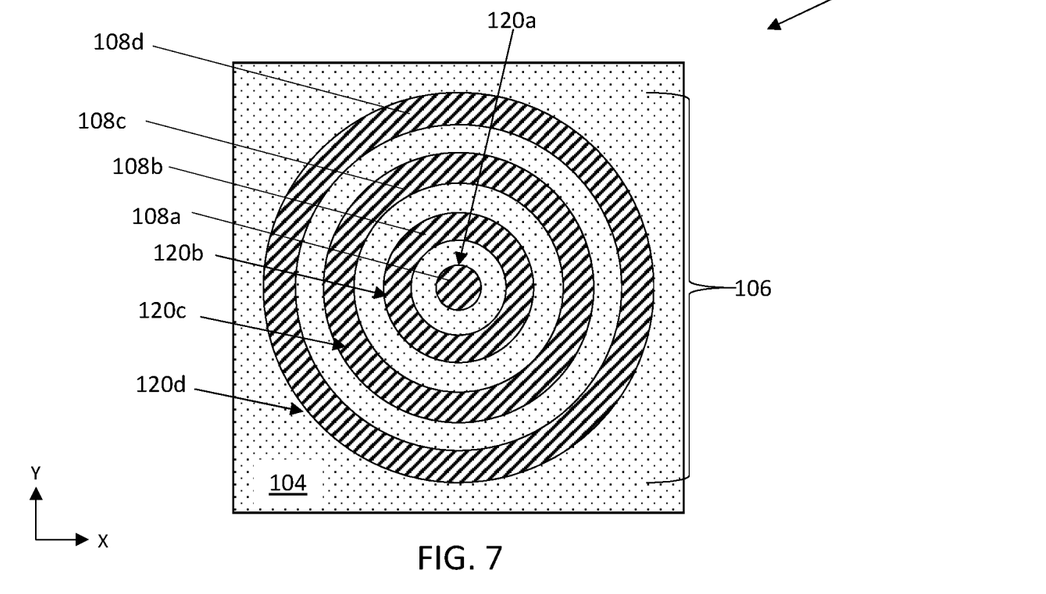
FIG. 7 shows a plan view in plane X-Y of a substrate structure spatial arrangement with multiple rounded trenches according to embodiments of the disclosure.

Turning now to FIGS. 6 and 7, further embodiments of the disclosure include forming first plurality of trenches 106 to have a spatial arrangement for focusing light at a center of substrate structure 100. According to this example, most of first plurality of trenches 106 may exhibit a looped shape. As discussed in further detail herein, it is understood that the smallest regions of first metal(s) 108 in substrate structure 100 may be positioned laterally within the interior of other first metal(s) 108 having a hollow interior and larger perimeter or circumference than first metal(s) 108 enclosed therein. It is also understood that each of the various embodiments of substrate structure 100 may be formed in multiple layers, e.g., as discussed relative to FIGS. 3-5 herein, and that only first plurality of trenches 106 is shown for clarity of illustration.

FIGS. 6 and 7 provide embodiments of substrate structure 100 in which first plurality of trenches 106 includes four trenches 120a, 120b, 120c, 120d each having a respective region of first metal 108 therein, denoted separately in each figure as regions 108a, 108b, 108c, 108d, and positioned within first dielectric layer 104. The embodiments of substrate structure 100 shown in FIGS. 6 and 7 and discussed herein are structured to focus light onto the innermost regions of first metal 108 in first dielectric layer 104 by a spatial arrangement in which first plurality of trenches 106 form a bull-eye type arrangement of first metal(s) 108. First metal 108a of first trench 120a, the innermost region of metal, is formed within a trench to have a substantially quadrilateral (FIG. 6) or rounded (FIG. 7) profile and an outer perimeter (FIG. 6) or outer circumference (FIG. 7). First metal 108a and first trench 120a may be laterally enclosed within portions of first dielectric layer 104 and structurally isolated from first metals 108b, 108c, 108d, and trenches 120b, 120c, 120d as shown. Second trench 120b with a portion of first metal 108b therein may also exhibit a substantially quadrilateral profile (FIG. 6) or rounded profile (FIG. 7) centered about and a hollow lateral interior for enclosing first metal 108a of first trench 120a and portions of first dielectric layer 104 laterally therein. As shown, second trench 120b may be positioned laterally outside the perimeter (FIG. 6) or circumference (FIG. 7) of first trench 120a where first metal 108a is formed. Substrate structure 100 may further include one or more regions of first metal identified as 108c, 108d within a third trench 120c and a fourth trench 120d, respectively. Trenches 120c, 120d in turn may be positioned laterally outside of first metals 108a, 108b and corresponding portions of first dielectric layer 104. Each region of first metal 108a, 108b, 108c, 108d and their corresponding trenches 120a, 120b, 120c, 120d are formed to be substantially concentric with each other. Thus, substrate structure 100 may include multiple trenches 120a, 120b, 120c, 120d and corresponding first metals 108a, 108b, 108c, 108d arranged to focus light onto first metal 108a of first trench 120a, i.e., the laterally innermost region of metal in substrate structure 100.

Figure 8:
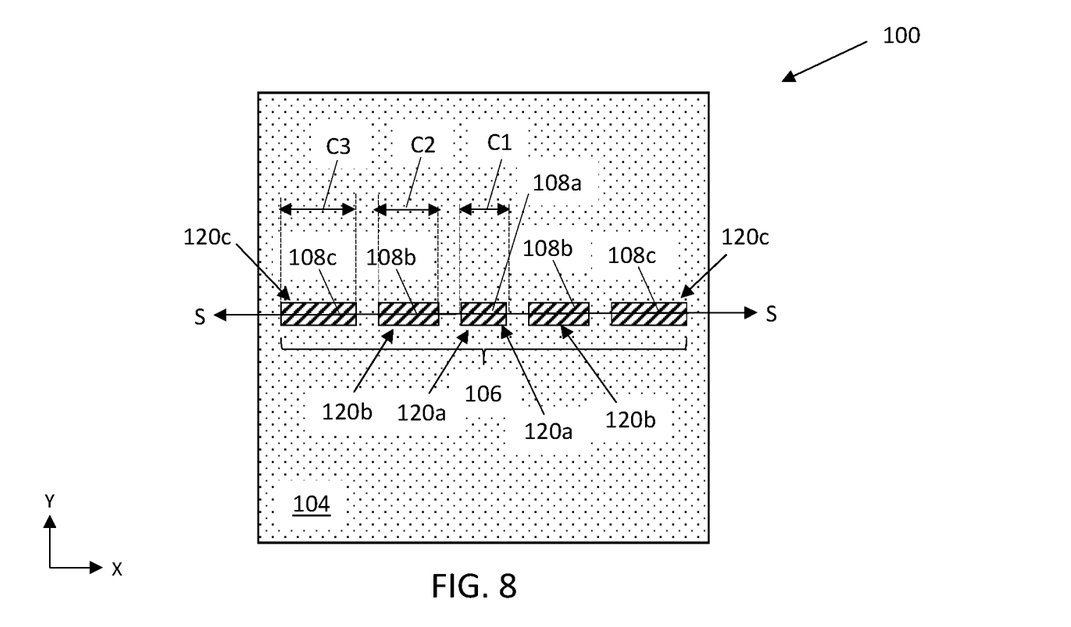
FIG. 8 shows a plan view in plane X-Y of a substrate structure spatial arrangement with multiple trench segments according to embodiments of the disclosure.

Turning to FIG. 8, embodiments of the disclosure provide other arrangements of trenches 120a, 120b, 120c configured to focus incident light onto portions of first metal 108a within a first trench 120a positioned at the laterally innermost location of substrate structure 100. In this case, first trench 120a is not wholly laterally enclosed by second and third trenches 120b, 120c. Instead, each trench 120a, 120b, 120c is shown to be oriented substantially along a shared axis S-S, with first trench 120a being positioned between pairs of second trenches 120b and third trenches 120c. According to an embodiment, first plurality of trenches 106 may include first trench 120a having a first length C1, second trench 120b extending substantially coaxially with first trench 120a and having a second length C2, and third trench 120c extending substantially coaxially with trenches 120a, 120b and having a third length C3. As shown, the laterally innermost trench 120a with first metal 108a therein may have the smallest of the three lengths C1, C2, C3 along X-axis. Furthermore, first trench 120a may be positioned substantially equidistantly between second trenches 120b, such that a substantially same lateral thickness of first dielectric layer 104 separates first trench 120a from second trenches 120b. Second trenches 120b may similarly be positioned equidistantly between first trench 120a and one third trench 120c.

Figure 9:
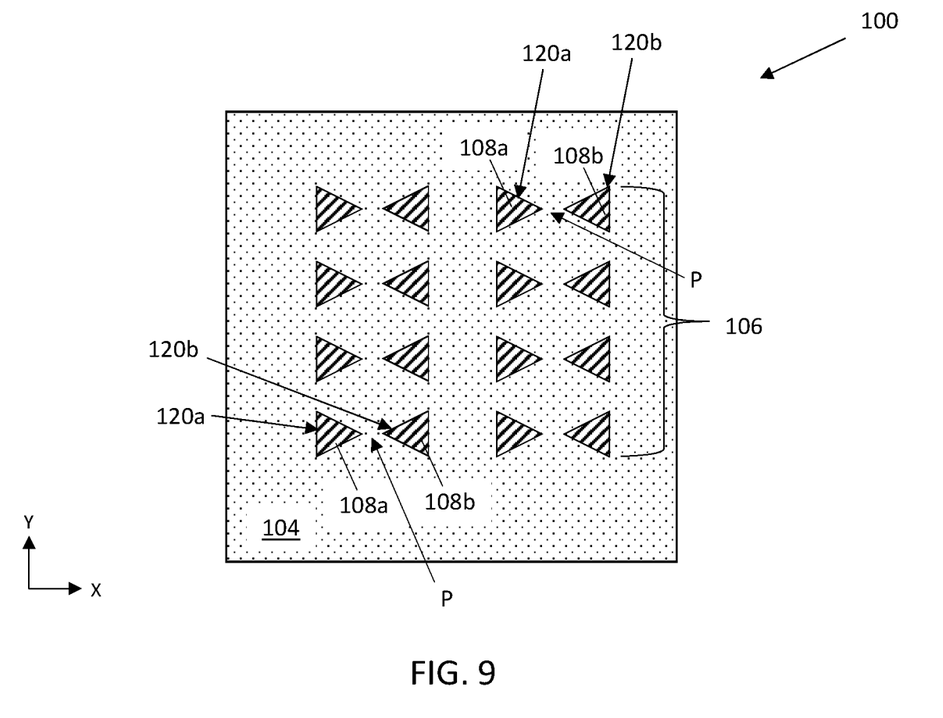
FIG. 9 shows a plan view in plane X-Y of a substrate structure spatial arrangement with inwardly tapered lateral sidewalls according to embodiments of the disclosure.

Turning to FIG. 9, another spatial arrangement of substrate structure 100 according to embodiments of the disclosure is shown. In the example of FIG. 9, regions of first metal 108a, 108b are formed respectively within first trench 120a and second trench 120b. Trenches 120a, 120b may each be one of a corresponding pair, and may feature an inwardly tapered shape to focus light to innermost portions of each pair of first metal regions 108a, 108b of substrate structure 100. First and second trenches 120a, 120b are shown by example as having a substantially triangular shape in plane X-Y, but this is not necessarily the case in all embodiments. More generally, first and second trenches 120a, 120b may feature inwardly tapered lateral sidewalls which meet at a convergence point P positioned proximate the other trench 120a, 120b of a given pair. The laterally tapered sidewalls of each trench 120a, 120b may be positioned proximate each other, e.g., are only separated from each other by portions of first dielectric layer 104 and no other intervening portions of first metal(s) 108a, 108b. To maintain the excitation of surface plasmons in first metal(s) 108a, 108b as discussed herein, pairs of first and second trenches 120a, 120b may not intersect with each other in the embodiment of FIG. 9.

Figure 10:
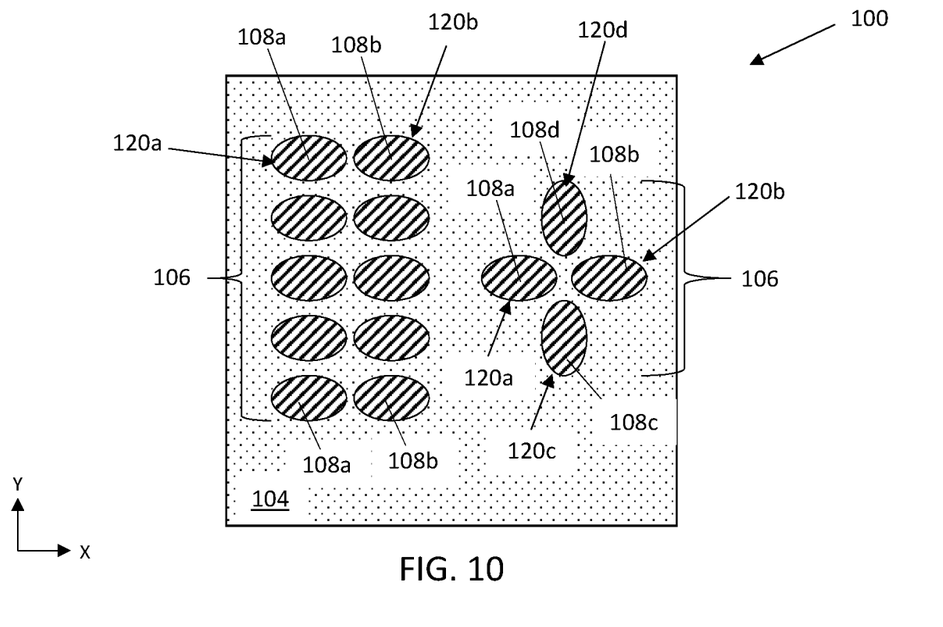
FIG. 10 shows a plan view in plane X-Y of a substrate structure spatial arrangement with substantially elliptical trenches according to embodiments of the disclosure.

Turning to FIG. 10, embodiments of substrate structure 100 may include groups or pairs of trenches 120a, 120b, 120c, 120d with substantially rounded geometries in place of laterally tapered sidewalls. As shown in FIG. 10, a pair of first and second trenches 120a, 120b and regions of first metal 108a, 108b therein may exhibit a substantially rounded or elliptical shape. In the case of an elliptical shape, each first trench 120a, 120b may have a major axis and a minor axis in plane X-Y. Pairs of trenches 120a, 120b and the regions of first metal 108a, 108b may be substantially coaxial with each other along a particular axis, e.g., the major or minor axis in the case of elliptical trenches 120a, 120b. Similar to other embodiments, first and second trenches 120a, 120b may not intersect with each other and thus may be separated by an intervening lateral portion of first dielectric layer 104. In any case, pairs of trenches 120a, 120b may be positioned such that an arc of one trench 120a curves toward the arc of another trench 120b, thereby focusing light to the lateral ends where trenches 120a, 120b are closest to each other.

With continued reference to FIG. 10, another spatial arrangement of trenches 120a, 120b, 120c, 120d in substrate structure 100 is described for the sake of example. According to a further example, trenches 120a, 120b, 120c, 120d may be provided in a group of four, with each trench 120a, 120b, 120c, 120d having a region of first metal 108a, 108b, 108c, 108d formed therein. Where four trenches 120a, 120b, 120c, 120d with rounded or elliptical shapes are included, two of the four trenches 120a, 120b may be substantially aligned with each other along a first axis (e.g., in parallel with X-axis as shown in FIG. 10). Another two of the four trenches 120c, 120d may be oriented substantially perpendicularly with respect to trenches 120a, 120b and substantially aligned with each other along another axis (e.g., in parallel with Y-axis as shown FIG. 10). Notwithstanding the presence of two additional trenches 120c, 120d, trenches 120a, 120b, 120c, 120d and regions of first metal 108a, 108b, 108c, 108d formed therein may not physically intersect with each other. Thus, substrate structure 100 may focus light toward portions of each trench 120a, 120b, 120c, 120d positioned closest to the other trenches 120a, 120b, 120c, 120d in substrate structure 100.

Figure 11:
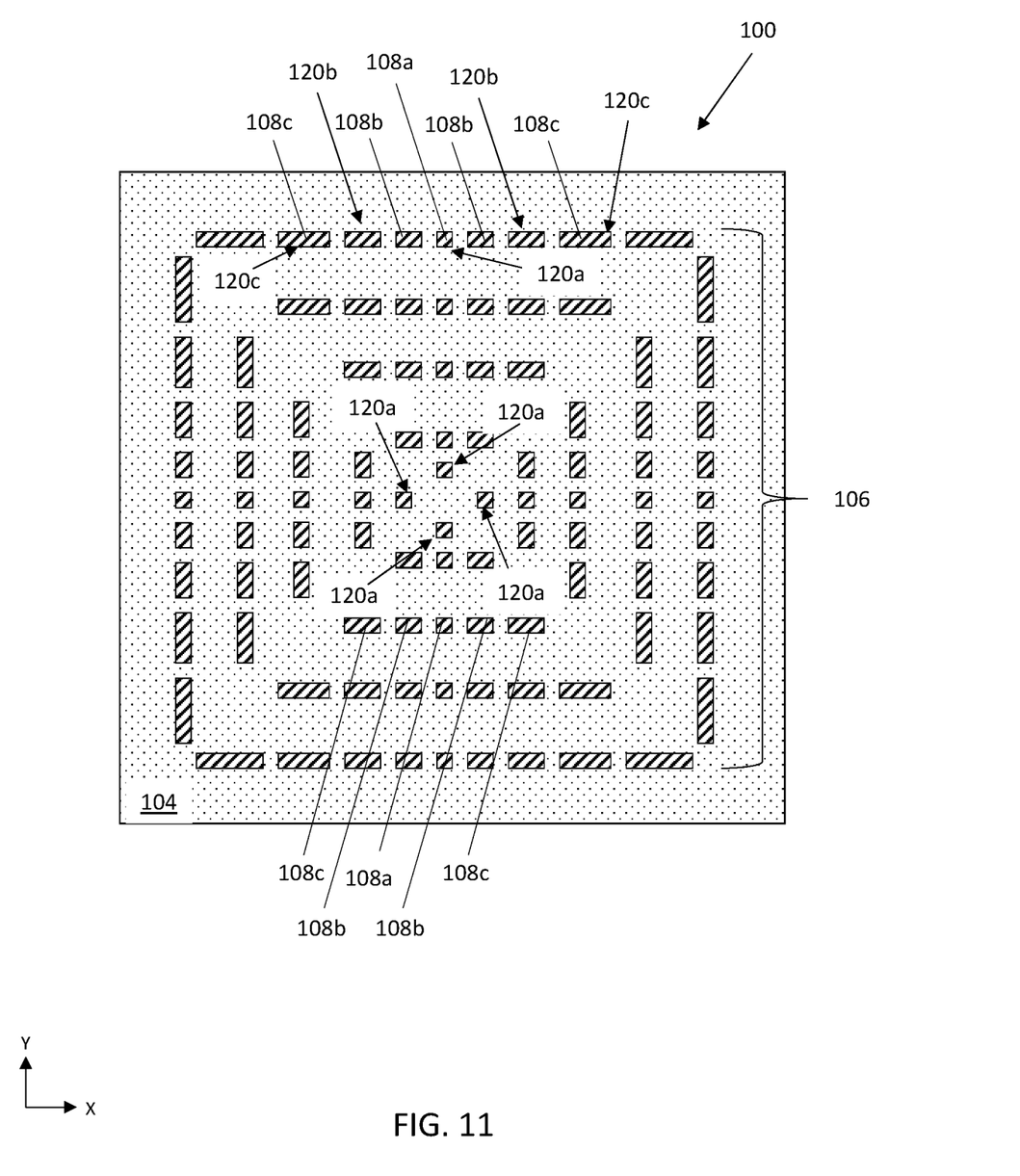
FIG. 11 shows a plan view in plane X-Y of a substrate structure spatial arrangement with multiple quadrilateral trenches and trench segments according to embodiments of the disclosure.

Turning to FIG. 11, it is emphasized that the various embodiments of substrate structure 100 may be used together and/or combined to include various features discussed herein relative to one or more other embodiments of substrate structure 100. FIG. 11, as an example, combines the features discussed elsewhere herein relative to FIGS. 6 and 8 into a single embodiment of substrate structure 100. According to an example, first plurality of trenches 106 may include coaxially-aligned rows of first trenches 120a, 120b, 120c in substantially quadrilateral outline and with successively smaller perimeters based on proximity to the lateral center of substrate structure 100. According to the example of FIG. 11, each first trench 120a in a particular row may be aligned with and positioned directly between a pair of second trenches 120b, and furthermore may be substantially equidistant from each second trench 120b. Second trenches 120b themselves may be positioned directly between, and equidistant from, first trench 120a and one third trench 120c. The various sets of trenches 120a, 120b, 120c with regions of first metal 108a, 108b, 108c therein may be arranged in quadrilateral sets having gradually decreasing perimeters. A centermost portion of substrate structure 100 may include one or more first trenches 120a for focusing light from regions of first metal 108a, 108b, 108c in surrounding trenches 120a, 120b, 120c and thus allowing for wavelengths of incident light to be coupled to surface plasmons near the center of substrate structure 100. Though rectangular trenches 120a, 120b, 120c and quadrilateral groups of trenches 120a, 120b, 120c are shown by example in FIG. 11, it is understood that rounded, triangular, and/or other geometrical profiles may be used in place of the specific profiles and/or spatial arrangements shown by example in FIG. 11.

Figure 12:
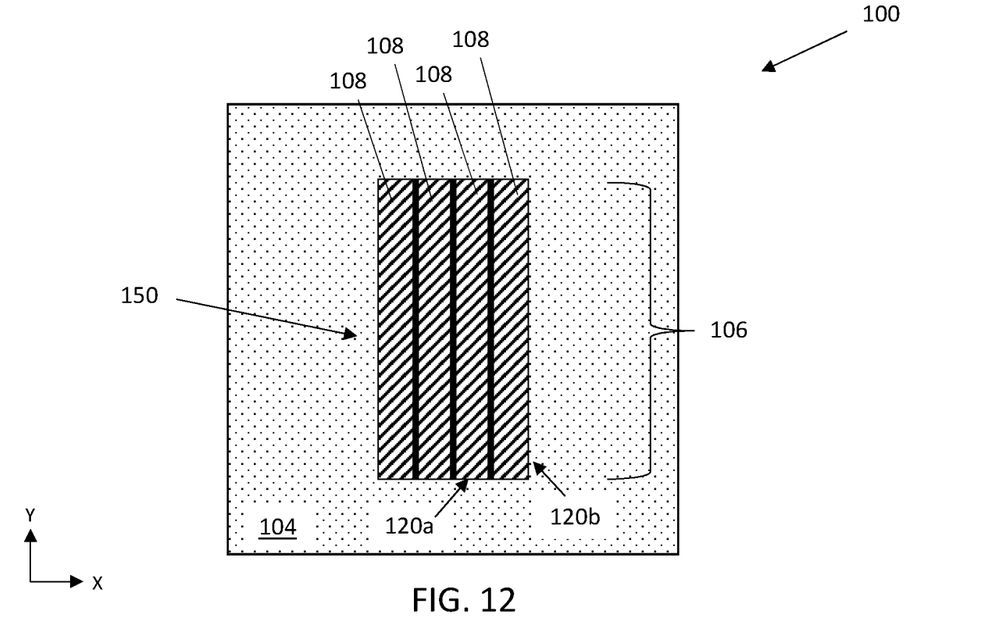
FIG. 12 shows a plan view in plane X-Y of a marking region for a substrate structure with substantially triangular trenches and ridges according to embodiments of the disclosure.
Figure 13:
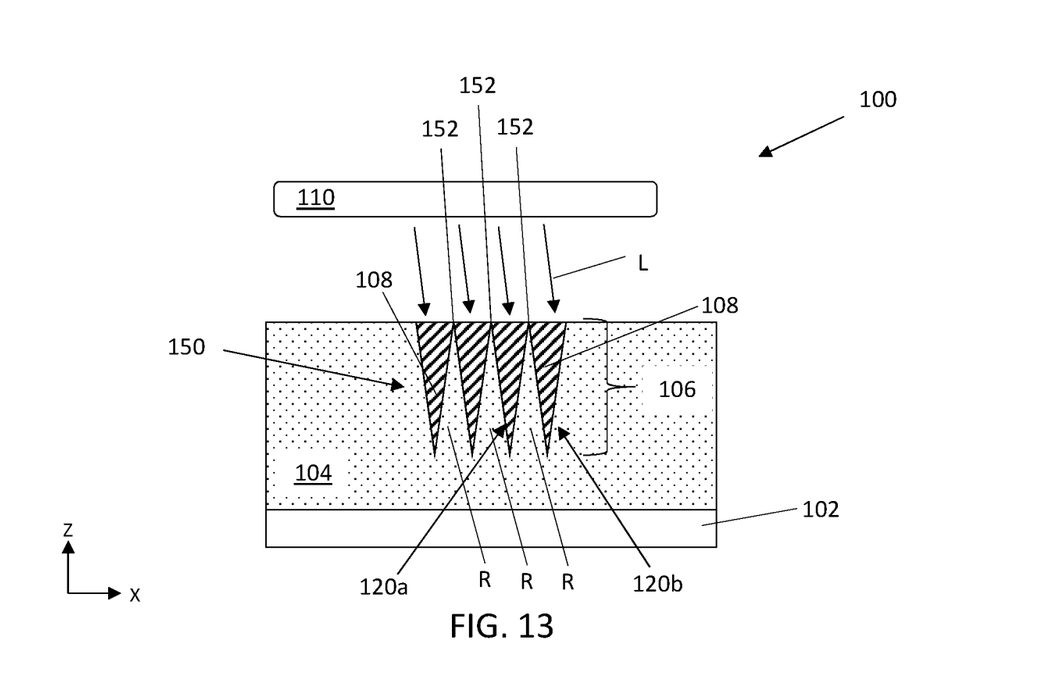
FIG. 13 shows a cross-sectional view in plane X-Z of a marking region for a substrate structure with substantially triangular trenches and ridges according to embodiments of the disclosure.
Figure 14:
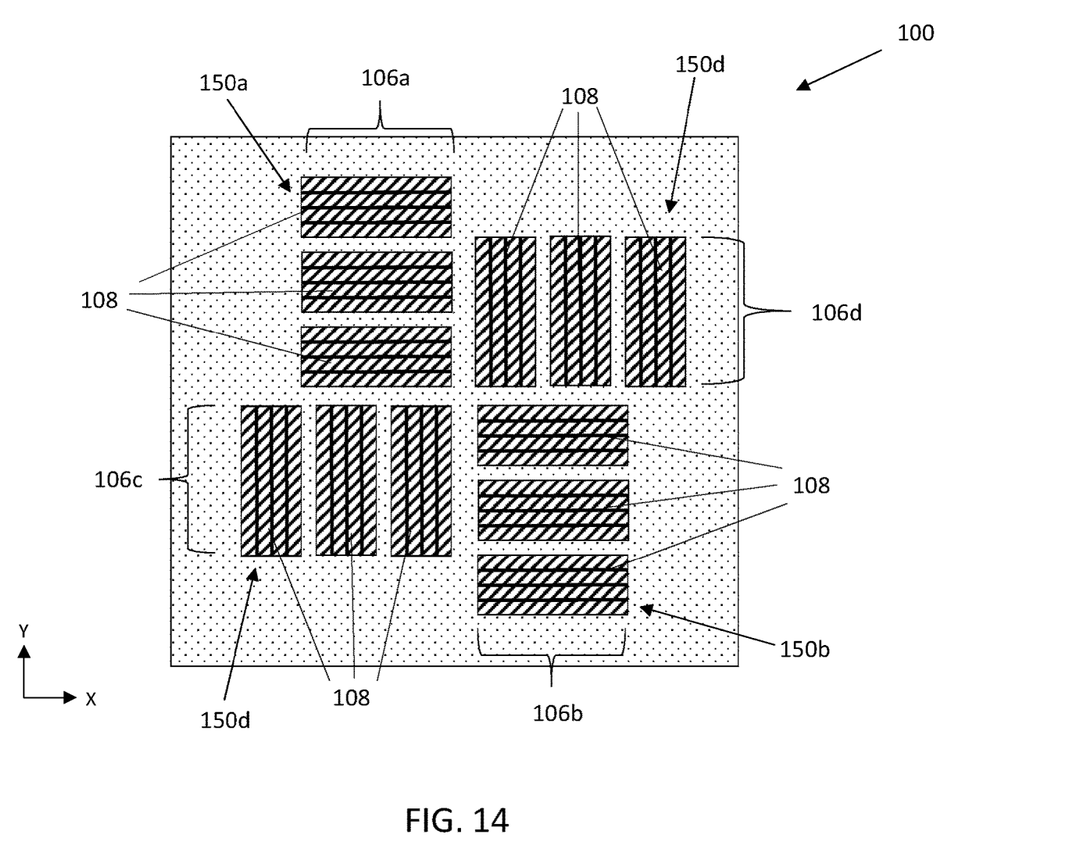
FIG. 14 shows a plan view in plane X-Y of a substrate structure with multiple marking regions according to embodiments of the disclosure.
Figure 15:
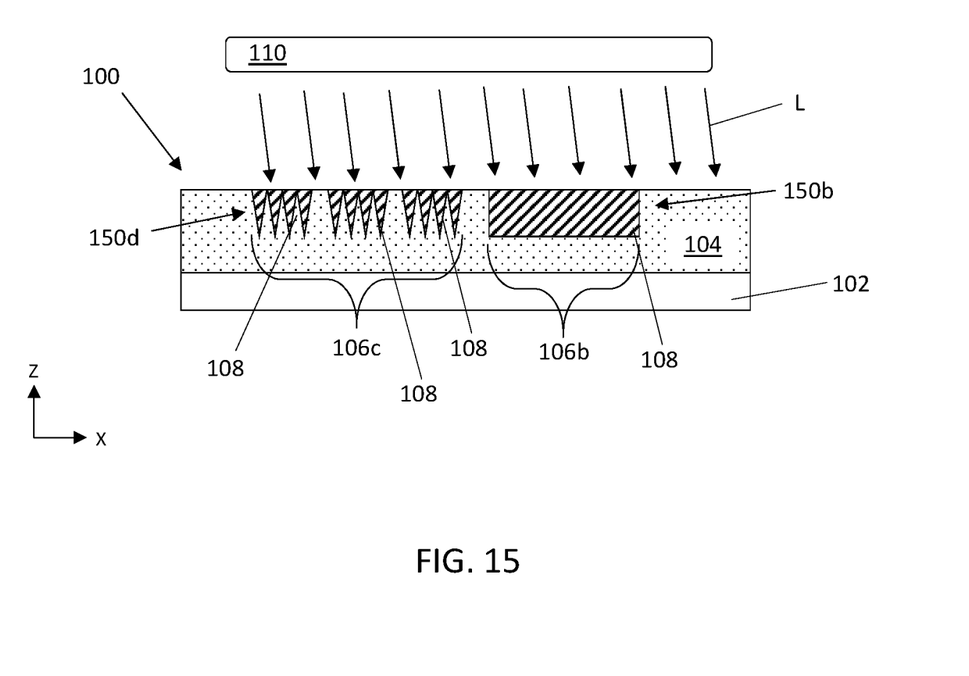
FIG. 15 shows a cross-sectional view in plane X-Y of a substrate structure with multiple marking regions according to embodiments of the disclosure.

Referring now to FIGS. 12 and 13, embodiments of substrate structure 100 may be structured for focusing light in a vertical direction to provide coupling of incident light to surface plasmons at vertical ends of first metal 108. Such embodiments may be used in addition to or in place of other embodiments discussed herein, e.g., which may be structured for coupling of incident light to surface plasmons at lateral ends of first metal(s) 108. FIG. 12 provides a plan view in plane X-Y of substrate structure 100 according to further embodiments, while FIG. 13 provides a cross-sectional view of the same embodiment of substrate structure 100 in plane X-Z. Embodiments of substrate structure 100 additionally may be grouped into one or more marking regions 150 as discussed herein, e.g., to provide several regions each configured to couple incident light with surface plasmons in substrate structure 100. A single marking region 150 is shown in FIGS. 12 and 13, while other embodiments of substrate structure 100 with multiple marking regions 150 are shown in FIG. 14 and discussed elsewhere herein.

Substrate structure 100 may include, e.g., first plurality of trenches 106 each having region of first metal 108 therein. First plurality of trenches may include at least one first trench 120a and at least one second trench 120b each with a longitudinal orientation (e.g., substantially parallel with Y-axis in FIG. 12). First and second trenches 120a, 120b may be positioned directly laterally adjacent to each other, and it is possible for portions of first metal 108 in each trench 120a, 120b to contact each other at an upper surface of first dielectric layer 104. First and second trenches 120a, 120b may exhibit a substantially triangular cross-section as shown specifically in FIG. 13. The various trenches 120a, 120b in substrate structure 100 may further include a substantially horizontal base located on one vertical end of first dielectric layer 104, and a tip (e.g., a convergence of inwardly tapered sidewalls) at their opposing vertical ends. According to the example of FIG. 13, each trench 120a, 120b may have a vertically-downward orientation, but it is understood that opposing vertical orientations are possible in further embodiments of the disclosure. The inward tapering of each trench 120a, 120b and first metal(s) 108 formed therein may be configured for the coupling of surface plasmons in first metal(s) 108 to particular wavelengths of incident light L. Specifically, the gradual reduction in trench width may allow for focusing of incident light L at the vertical tip of each trench 120a, 120b and an associated coupling of surface plasmons in first metal(s) 108 to incident light L.

The structural configuration of trenches 120a, 120b and first metal 108 therein may determine the shape of nearby portions of first dielectric layer 104. First and second trenches 120a, 120b being positioned directly adjacent to each other may form, e.g., a ridge R within first dielectric layer 104. Ridge R, as shown in FIG. 13, may exhibit a substantially triangular cross-section with an opposite orientation to that of trenches 120a, 120b. In this case, ridge(s) R may feature a tip 152 positioned at or near the upper horizontal surface of first dielectric layer 104 due to the tapered sidewalls of each trench 120a, 120b. Where multiple substantially triangular trenches 120a, 120b appear in substrate structure 100, one ridge R may appear in first dielectric layer 104 between first metals 108 of each pair of trenches 120a, 120b. As noted above, it is possible for tip 152 of ridge(s) R to be positioned vertically beneath the upper horizontal surface of first dielectric layer 104.

Referring now to FIGS. 12-15, a single group of trenches 120a, 120b and first metal 108 formed therein may constitute a single marking region 150 of substrate structure 100 as discussed elsewhere herein. According to an embodiment, one marking region 150 may be defined as including all trenches 120a, 120b and region of first metal 108 having the same lateral orientation (i.e., in plane X-Y). To provide more robust detectability of substrate structure 100, embodiments of the disclosure contemplate forming multiple marking regions 150a, 150b, 150c, 150d (FIGS. 14, 15 only) in a single substrate structure 100. According to an example, each marking region 150a, 150b, 150c, 150d may include several groups of paired trenches 120a, 120b (identified separately in FIGS. 12, 13) each having regions of first metal 108 formed therein. The various trenches 120a, 120b in each marking region 150a, 150b, 150c, 150d may exhibit a substantially triangular cross-section as noted elsewhere herein.

One or more marking regions 150 may have a different longitudinal orientation from that of other marking regions. For instance, marking regions 150a, 150b are each shown to have a respective plurality of trenches 106a, 106b oriented along the same axis (e.g., in parallel with X-axis), while being located in different areas of first dielectric layer 104 and/or substantially in parallel with each other. Other marking regions 150c, 150d, are shown by example to have substantially the same lateral surface area as marking regions 150a, 150b but different lateral orientations. Marking regions 150c, 150d may be oriented substantially perpendicularly with respect to marking regions 150a, 150b (e.g., in parallel with Y-axis), but substantially in parallel with each other. Each marking region 150a, 150b, 150c, 150d may include a set of ridges R (FIG. 13 only) directly between each pair of trenches 120a, 120b (FIGS. 12, 13) as discussed elsewhere herein. As also shown in FIG. 14, it is possible to include a larger amount of separation between two or more regions of first metal 108, e.g., such that each plurality of trenches 106a, 106b, 106c, 106d may be subdivided into groups of two, four (as shown in FIG. 14), six, etc. Substrate structure 100 according to the disclosure thus may include first pluralities of trenches 106 and first metal(s) 108 therein, and with various spatial arrangements for coupling surface plasmons in first metal(s) 108 to one or more wavelengths of incident light.

It is again emphasized that the various embodiments of substrate structure 100 discussed herein and illustrated in FIGS. 1-14 are not limited to a single type of spatial arrangement, or being formed in only one layer of a particular IC structure. For example, it is possible to form and use an embodiment of substrate structure 100 in every single distinct layer of an IC structure, and in multiple locations within the same layer of a particular structure. Furthermore, it is possible for one or more embodiments of substrate structure 100 to be placed in substantial vertical alignment with a similar or different embodiment of substrate structure 100 in a different layer of the same IC structure. Various embodiments substrate structure 100 may also be modified to include still other spatial arrangements configured for coupling of surface plasmons in first metal 108 and/or other metals of different layers to particular wavelengths of incident light. The various embodiments of substrate structure 100 may also be combined with each other to form still further embodiments, or selected portions of substrate structure 100 may be omitted to provide a simplified marking structure. In any case, substrate structure 100 may be operable to couple surface plasmons in a metal substance to wavelengths of incident light by being structured to focus the incident light into areas with a lowest length, surface area, volume, etc., in horizontal and/or vertical directions.

The terminology used herein is for the purpose of describing particular embodiments only and is not intended to be limiting of this disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s). "Substantially" refers to largely, for the most part, entirely specified or any slight deviation which provides the same technical benefits of this disclosure.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to this disclosure in the form disclosed. Many modifications and variations will be apparent to those of ordinary skill in the art without departing from the scope and spirit of this disclosure. The embodiment was chosen and described in order to best explain the principles of this disclosure and the practical application, and to enable others of ordinary skill in the art to understand this disclosure for various embodiments with various modifications as are suited to the particular use contemplated.

Unless otherwise noted, or as may be evident from the context of their usage, any terms, abbreviations, acronyms or scientific symbols and notations used herein are to be given their ordinary meaning in the technical discipline to which the disclosure most nearly pertains. The following terms, abbreviations and acronyms may be used throughout the descriptions presented herein and should generally be given the following meaning unless contradicted or elaborated upon by other descriptions set forth herein. Some of the terms set forth below may be registered trademarks (®).

What is claimed is:

1. A method of detecting overlay alignment when fabricating an integrated circuit (IC) structure, the method comprising:
   providing a substrate structure, the substrate structure including:
      a first dielectric layer positioned above a semiconductor substrate;
      a first plurality of trenches within an upper surface of the first dielectric layer; and
      a first metal within the first plurality of trenches, wherein a spatial arrangement of the first plurality of trenches causes coupling of surface plasmons in the first metal to at least one wavelength of an incident light;
   illuminating the substrate structure with a light source including wavelength components which couple with surface plasmons in the first metal, and wherein the illuminating yields focused plasmons within the substrate structure; and
   detecting the overlay alignment by detecting the incident light reflected from the substrate structure.

2. The method of claim 1, wherein the light source has a maximum emission at the wavelength components which resonate with the substrate structure, such that the light source creates focused plasmons within the substrate structure during the illuminating.

3. The method of claim 1, wherein the light source is substantially monochromatic at the wavelength components which resonate with the substrate structure such that the light source creates focused plasmons within the substrate structure during the illuminating.

4. The method of claim 1, wherein an incident angle of the illumination is substantially perpendicular to an upper surface of the substrate structure.

5. The method of claim 1, wherein an incident angle of the illumination is in the range of between approximately 5 degrees to approximately 90 degrees from perpendicular relative to an upper surface of the substrate structure.

6. The method of claim 1, further comprising:
   forming an intermediate layer above the substrate structure; and
   forming a second substrate structure on an upper surface of the intermediate layer, wherein the second substrate structure is positioned above, and substantially vertically aligned with, the substrate structure.

7. The method of claim 1, wherein the light source emits light including components having a wavelength in the range of between approximately 400 nanometers (nm) to approximately 700 nm.

* * * * *